(12) United States Patent
Lomax et al.

(10) Patent No.: US 8,147,882 B2
(45) Date of Patent: Apr. 3, 2012

(54) HERBAL PAIN KILLER COMPOSITIONS

(76) Inventors: Leonard Lomax, Elkins Park, PA (US); Kory Pohlman, West Des Moines, IA (US)

( * ) Notice: Subject to any disclaimer, the term of this patent is extended or adjusted under 35 U.S.C. 154(b) by 0 days.

(21) Appl. No.: 12/895,200

(22) Filed: Sep. 30, 2010

(65) Prior Publication Data

US 2011/0076327 A1 Mar. 31, 2011

Related U.S. Application Data

(60) Provisional application No. 61/247,517, filed on Sep. 30, 2009.

(51) Int. Cl.
*A61K 36/76* (2006.01)
*A61K 36/324* (2006.01)
*A61K 36/756* (2006.01)
*A61K 36/9066* (2006.01)

(52) U.S. Cl. .......... 424/756; 424/725; 424/769

(58) Field of Classification Search .......... None
See application file for complete search history.

(56) References Cited

U.S. PATENT DOCUMENTS

| | | | |
|---|---|---|---|
| 3,932,628 A | 1/1976 | Hudson | |
| 5,888,514 A | 3/1999 | Weisman | |
| 5,908,628 A * | 6/1999 | Hou | 424/735 |
| 6,197,307 B1 | 3/2001 | Wheatley et al. | |
| 6,224,871 B1 | 5/2001 | Hastings et al. | |
| 6,280,737 B1 | 8/2001 | Stumpf et al. | |
| 6,333,056 B1 | 12/2001 | Robinson | |
| 6,340,480 B1 | 1/2002 | Duckett et al. | |
| 6,534,086 B1 | 3/2003 | Krumhar | |
| 6,541,045 B1 | 4/2003 | Charters et al. | |
| 6,746,695 B1 | 6/2004 | Martin et al. | |
| 6,777,441 B2 | 8/2004 | Wang et al. | |
| 6,812,214 B2 | 11/2004 | Shin et al. | |
| 6,949,260 B2 | 9/2005 | Krumhar | |
| 7,056,539 B2 | 6/2006 | Leko | |
| 7,112,578 B2 | 9/2006 | Levin | |
| 7,229,648 B2 | 6/2007 | Dreyer | |
| 7,232,585 B2 | 6/2007 | Quan et al. | |
| 7,282,224 B1 | 10/2007 | Roederer | |
| 7,297,352 B1 | 11/2007 | Free | |
| 7,455,860 B2 | 11/2008 | Gokaraju et al. | |
| 7,507,424 B2 | 3/2009 | Mitra et al. | |
| 2004/0081664 A1 | 4/2004 | Gow et al. | |
| 2004/0086581 A1* | 5/2004 | Jones | 424/756 |
| 2005/0084547 A1 | 4/2005 | Subbiah | |
| 2006/0024397 A9 | 2/2006 | Nair et al. | |
| 2006/0062859 A1 | 3/2006 | Blum et al. | |
| 2007/0036834 A1 | 2/2007 | Pauletti et al. | |
| 2009/0082738 A1 | 3/2009 | Vad | |
| 2009/0092668 A1 | 4/2009 | Finkelstein | |
| 2009/0156666 A1 | 6/2009 | Raederstorff et al. | |
| 2009/0197957 A1 | 8/2009 | Selley et al. | |

FOREIGN PATENT DOCUMENTS

| | | |
|---|---|---|
| DE | 3316726 A1 | 11/1984 |
| DE | 19603788 B4 | 8/1997 |
| DE | 10143146 B4 | 3/2003 |
| EP | 0524873 A1 | 1/1993 |
| EP | 1210945 A1 | 11/2001 |
| FR | 2605224 | 4/1988 |
| FR | 2614791 | 11/1988 |
| FR | 2753374 | 3/1998 |
| FR | 2773484 | 7/1999 |
| GB | 2335919 A | 10/1999 |
| JP | 2001346545 | 12/2001 |
| WO | WO98/52583 | 11/1998 |
| WO | WO03/103694 A1 | 12/2003 |
| WO | WO2004/062639 A1 | 7/2004 |

OTHER PUBLICATIONS

L. Yin et al., 'Simultaneous determination of 11 active components in two well-know traditional Chinese medicines by HPLC coupled with diode array detection for quality control', Journal of Pharmaceutical and Biomedical Analysis, vol. 49, No. 4, pp. 1101-1108 (May 11, 2009).
C. Chrubasik et al., 'Impact of Herbal Medicines on Physical Impairment', Phytomedicine4, vol. 15, No. 6-7, pp. 536-539 (Jun. 2008).
C. Lans, 'Ethomedicines used in Trinidad and Tobago for reproductive problems', Journal of Ethnobiology and Ethnomedicine, vol. 3, No. 13., pp. 1-12 (Mar. 15, 2007).
PCT Transmittal of International Search Report and Written Opinion, Jul. 12, 2011, 16 pages.

* cited by examiner

*Primary Examiner* — Susan Hoffman
(74) *Attorney, Agent, or Firm* — PCT Law Group, PLLC

(57) ABSTRACT

Disclosed are natural compositions including at least five core ingredients that provide pain relief without the side effects of synthetic pain relievers. Further provided are methods of making the disclosed herbal formulations or compositions, and methods of treating mammals that include administering the herbal compositions to a mammal in need thereof.

17 Claims, 3 Drawing Sheets

Onset of Analgesic Effect

HERBAL PAIN KILLER COMPOSITIONS

This application claims the benefit of priority to U.S. Provisional Patent Application Ser. No. 61/247,517, filed Sep. 30, 2009.

TECHNICAL FIELD

The present embodiments relate generally to herbal pain killer compositions and to methods of making and using such compositions.

BACKGROUND

People of all ages, genders and races suffer at some point from various types of pain. This ranges from general muscle aches and headaches, to significant pain from arthritis, acute injuries, surgery related pain as well as pain from chronic conditions. Chronic pain is the leading cause of adult disability in the United States and is one of the most common reasons for patient visits to primary care clinicians. (Leigh J P, Markowitz S B, Fahs M, Shin C, Landrigan P J. Occupational injury and illness in the United States: estimates of costs, morbidity, and mortality. Arch Intern Med 1997; 157:1557-68.)

Conventional treatment with prescribed and over the counter (OTC) drugs such as acetaminophen (Tylenol) or non-steroidal anti-inflammatory drugs (NSAIDs, such as ibuprofen (e.g., Motrin and Advil) and naproxen (e.g., Aleve and Naprosyn)), COX-2 inhibitor's (e.g., Celebrex), and narcotics have remained the mainstay of current treatments. However, these treatments are typically associated with significant adverse side effects (e.g., gastrointestinal, cardiovascular, and addiction).

NSAIDs are among the most frequently used class of drugs worldwide, with yearly over-the-counter sales amounting to $30 billion. Gastrointestinal safety continues to be a high priority for patients and clinicians when choosing an NSAID treatment for pain. In fact, the gastrointestinal harm induced by NSAIDs may be the most prevalent adverse event associated with any drug class. Clinical manifestations of adverse gastrointestinal events include gastric and duodenal mucosal erosions, ulcers and ulcer complications, dyspepsia, abdominal pain and nausea. Dyspeptic symptoms include epigastric pain, bloating, nausea and heartburn, which account for the most common reason for discontinuation of NSAID therapy. Gastric or duodenal ulceration occurs in about 20% of NSAID users, and 40% of these individuals develop a serious complication. Other problems in the lower gut linked to the use of NSAIDs are gut inflammation, increase in gut permeability, stricture, protein malabsorption, bleeding, and perforation. Therefore, as a result of the widespread use of these agents, the potential for a significant number of adverse events, particularly gastrointestinal related, is high. Gastrointestinal adverse events associated with NSAID use are reported to account for more than 100,000 hospitalizations and more than 15,000 deaths annually. Noteworthy are the numbers of hospitalizations for patients taking long-term, low-dose aspirin who are admitted with upper gastrointestinal bleeding. This accounts for about 10-15% of the hospital admissions for upper gastrointestinal bleeding. The resulting economic costs incurred in managing NSAID related gastrointestinal adverse events are significant; where it is estimated that $0.66-1.25 of every dollar spent on the cost of the NSAID is associated with treating adverse events.

Selective (COX-2) inhibitors have demonstrated improved gastrointestinal tract safety over traditional NSAIDs drugs. There is important evidence from clinical trials showing that compared with traditional NSAIDs, COX-2 inhibitors are associated with a reduced rate of serious GI events such as bleeding, perforation and obstruction, and other symptoms such as dyspepsia, as well as a reduced requirement for concomitant gastroprotective therapies such as proton pump inhibitors. This relative benefit may be related to a lack of COX-1-mediated inhibition of gastric mucous production and a lack of effect on platelet thromboxane production. However, the differential effects of COX-2 inhibitors compared with traditional NSAIDs on platelet aggregation, prostacyclin/thromboxane balance, and inflammatory mediators involved in the development of atherosclerosis have also led to concerns that there is a physiological basis for COX-2 inhibitors to increase the risk for thrombotic events. These negative cardiotoxic effects (myocardial infarctions) of the COX-2 inhibitors were first documented in the Vioxx Gastrointestinal Outcomes Research (VIGOR) trial and the Celecoxib Long-term Arthritis Safety Study (CLASS). Although the cardiotoxic effects were thought to be limited to myocardial infarctions, a subsequent meta analysis showed an increase in the occurrence of arrhythmias in COX-2 treated patients as well. The ensuing body of evidence relating to adverse cardiovascular outcomes prompted the FDA to remove rofecoxib (Vioxx®) from the market and led to modified warnings and use of Celecoxib (Celebrex®). Additionally, resulting changes to pain treatment recommendations have led to a significant decline in the use of the COX-2 inhibitors.

Because of the widespread use of NSAIDs and COX-2 inhibitors, the risks associated with their use are of increasing concern. In the recently concluded 2009 American Geriatrics Society (AGS) annual meeting; as a result of their troubling side effect profiles, the revised AGS guidelines on the management of persistent pain to be published in the August issue of the Journal of the American Geriatrics Society adopted the position and will advise physicians to have their elderly patients avoid the use of NSAIDs and COX-2 inhibitors and consider the use of low-dose opioid therapy instead. This position reflects general safety concerns with the use of these agents.

As the population ages, more patients will experience osteoarthritis, rheumatoid arthritis, chronic back pain, chronic musculoskeletal injuries, and migraines. Other ailments such as pain from overexertion, perimensual pain, etc, will also necessitate treatment. It is therefore very likely that gastrointestinal problems will continue to increase as the use of the traditional nonselective NSAIDs in the United States increases because of the concern for cardiovascular complications associated with the COX-2 inhibitors. The elderly are especially at risk for gastrointestinal events, including serious complications.

There therefore remains a need for just as effective, but safer alternatives for the treatment of pain.

Many anecdotal as well as recent studies support the use of natural remedies (herbal) for relief of pain. Historically herbal remedies have not only been reported as effective, but they have been used to treat various ailments and conditions and generally have had very low risk profiles. But such remedies are not typically as effective as pharmaceutical pain relief products that are currently available OTC or by prescription.

SUMMARY

Example embodiments are generally directed to compositions that include natural ingredients for the treatment of pain in mammals. In particular, according to non-limiting example embodiments, compositions provided herein may include Boswellia serrata, Harpagophytum procumbens (Devil's claw), Turmeric, White Willow, and Phellodendron amurense. According to example embodiments, the present compositions may include one or more additional ingredients such as synergistic ingredients selected from Chiococca Alba, Dihydroxybergamottin, Lactuca Virosa, Mimosa Pudica, Naringen, Paullinia Tomentosa, and Yerba Mate, and other ingredients having similar properties and/or effects. Also provided are compositions that may include one or more excipients.

According to non-limiting example embodiments, the present compositions help provide general analgesic relief of the pain associated with headaches, migraines, arthritis, toothaches, menstrual cramps, muscle aches, post operative surgical pain, strains, sprains, inflammation, chronic pain and other sources of pain.

Example compositions according to the present application are believed to be safer, more potent, and provide effective, lasting relief of pain from many conditions including for example, headaches, migraines, arthritis, toothaches, menstrual cramps, muscle aches, post operative surgical pain, strains, sprains, inflammation, chronic pain, etc.

According to other non-limiting example embodiments, methods are provided, which include administering an effective amount of the present compositions to a mammal in need thereof.

Further provided are methods of making the compositions provided herein.

BRIEF DESCRIPTION OF THE FIGURES

Embodiments of the invention are herein described, by way of non-limiting example, with reference to the following accompanying Figures.

DETAILED DESCRIPTION

Figure 1:
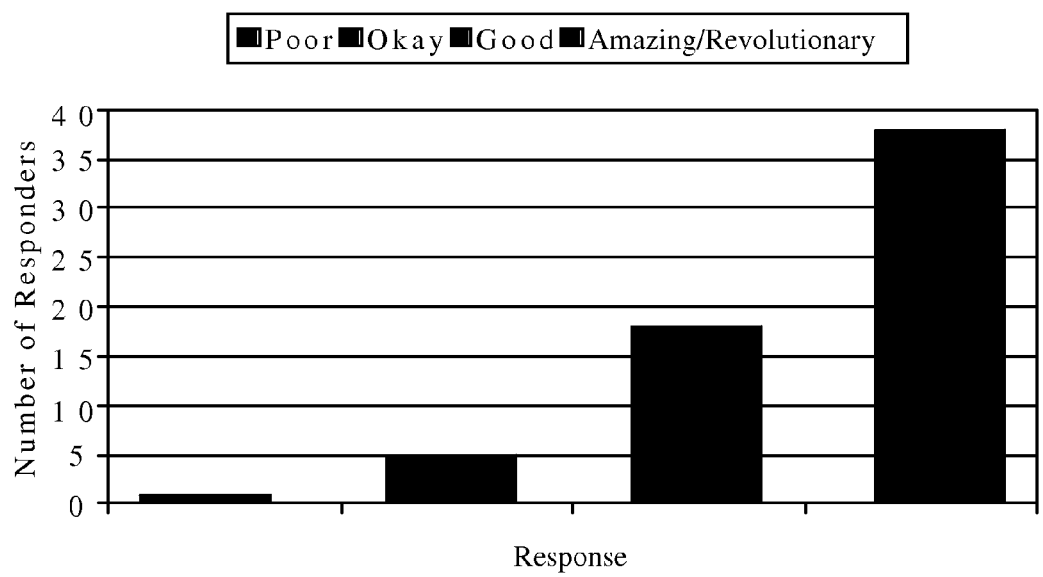
FIG. 1 is a graph showing patient response to treatment with the composition of Example 1.

Generally provided herein are various compositions and methods that provide general analgesic relief of pain for the treatment of pain in mammals. Present embodiments include methods of treating or preventing pain caused e.g., by headaches, including migraines, arthritis, toothaches, menstrual cramps, muscle aches, post operative surgical pain, strains, sprains, inflammation, including acute and chronic pain. Also included are methods of making the compositions herein.

Various combinations of natural products have been tried in the past, but the potency and effect of such products was not sufficient to replace prescription or over-the-counter ("OTC") pain reliever products that are synthetically derived in a laboratory. The present inventors discovered that particular combinations of ingredients have unexpectedly superior synergistic pain relieving effects. The potency of the present compositions is much higher for the general analgesic relief of pain than of prior natural products. Therefore, the present compositions can be used as a substitute for synthetic pain relievers, while retaining the safety of a natural product.

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

In describing example embodiments, specific terminology is employed for the sake of clarity. However, the embodiments are not intended to be limited to this specific terminology.

As used herein, "a" or "an" may mean one or more. As used herein, "another" may mean at least a second or more. Furthermore, unless otherwise required by context, singular terms include pluralities and plural terms include the singular.

As used herein, "composition", "therapeutic composition" and "formulation" may be used interchangeably and refer to a combination of elements that is presented together for a given purpose. Such terms are well known to those of ordinary skill in the art.

As used herein, the term "core ingredient" is intended to encompass those ingredients of the present composition that are the most important in the present compositions and methods. According to non-limiting example embodiments, compositions provided herein include at least the following five core ingredients, boswellia serrata, harpagophytum procumbens (devil's claw), turmeric, white willow and phellodendron amurense. According to other example embodiments, "core ingredients" may include one or more additional or different ingredients than those listed above, such as one or more synergistic ingredients or other natural ingredients that may be used to treat a mammal in need of treatment.

As used herein, the term "synergistic ingredient" is intended to encompass natural ingredients that are not necessarily "core ingredients" in the present compositions, but may be added to the present compositions for example to add to the pain relief that may be achieved by the compositions, or to add to the synergistic effects to be achieved by the present compositions, or to improve efficacy, etc. Non-limiting example embodiments of possible synergistic ingredients include one or more ingredients selected from Chiococca Alba, Dihydroxybergamottin, Lactuca Virosa, Mimosa Pudica, Naringen, Paullinia Tomentosa, and Yerba Mate. According to non-limiting example embodiments, Ulmus Glabra may be a synergistic ingredient, for example as a substitute for Paullinia Tomentosa.

The terms "drug" and "active ingredients" are used herein to include any drug or other active ingredient that may be added to the present compositions in addition to the core and synergistic ingredients for treating mammals for a variety of different conditions.

By way of non-limiting example embodiment, additional core ingredients or other drugs or active ingredients that may be added to the present compositions may include the addition of Bromelian, Green Tea (for example, replacing Yerba mate), and possibly Fish Oil, Lecithin, Essential Fatty acids, Magnesium and/or other minerals. These terms are not meant to be limiting and may include any "active ingredient" and "drug" known to those skilled in the art, which may be incorporated in the formulations herein.

The terms "core ingredients," "synergistic ingredients," and "active ingredients" and "drugs" are intended to encompass such ingredients in all forms including, but not limited to extracts, powders, analogs, prodrugs, salts, esters, polymorphs and/or crystalline forms thereof as would be apparent to those skilled in the art.

The term "excipient" is used herein to include pharmaceutically acceptable inert substances added to a drug formulation to give e.g., a desired consistency or form, or used as a carrier. Non-limiting examples of excipients that may be included in the present compositions and/or formulations herein may include, but are not limited to binders, fillers, diluents, lubricants, disintegrants, super-disintegrants, and other excipients known to those skilled in the art, depending e.g., on the composition being formed, method of formation, active ingredient(s) being used, etc.

As used herein, the term "binder" is intended to encompass binders known to those skilled in the art. The following is a list of non-limiting example embodiments of binders that may be used in accordance with various embodiments herein: acacia, alginic acid, carbomer (e.g., carbopol), carboxymethylcellulose sodium (CMC), dextrin, ethyl cellulose, gelatin, guar gum, hydroxyethyl cellulose (HEC), hydroxypropyl cellulose (e.g., Klucel) (HPC), hydroxypropyl methyl cellulose (e.g., Methoce HPMC), magnesium aluminum silicate, maltodextrin, methylcellulose, polymethacrylates, povidone (e.g., Kollidon, Plasdone PVP K29/32), pregelatinized starch, sodium alginate, starch and zein. As with other excipients herein, the amount of the binder may vary depending on various factors as would be known or can be determined by those skilled in the art.

As used herein, the terms "filler" and "diluent" are intended to encompass fillers known to those skilled in the art. The following is a list of non-limiting example fillers that may be used in accordance with various embodiments herein: microcrystalline cellulose, dextrose, calcium phosphate anhydrous, calcium carbonate, calcium sulfate, compressible sugars, dextrates, dextrin, dibasic calcium phosphate dihydrate, glyceryl palmitostearate, hydrogenated vegetable oil (type I), kaolin, lactose, magnesium carbonate, magnesium oxide, maltodextrin, mannitol, polymethacrylates, potassium chloride, powdered cellulose, pregelatinized starch, sodium chloride, sorbitol, starch, sucrose, sugar spheres, talc and tribasic calcium phosphate. The amount of the filler or diluent may vary depending on various factors as would be known or can be determined by those skilled in the art.

Other "fillers" may act for example, more as compression aids. The following is an additional list of such non-limiting example fillers that may be used in accordance with various embodiments herein: lactose, calcium carbonate, calcium sulfate, compressible sugars, dextrates, dextrin, dextrose, calcium phosphate, kaolin, magnesium carbonate, magnesium oxide, maltodextrin mannitol, powdered cellulose, pregelatinized starch, and sucrose. The amount of such fillers may vary depending on various factors as would be known or can be determined by those skilled in the art.

As used herein, the term "lubricant" is intended to encompass lubricants known to those skilled in the art. The following is a list of non-limiting example embodiments of lubricants that may be used in accordance with various embodiments herein: magnesium stearate, stearic acid, calcium stearate, glyceryl monostearate, glyceryl palmitostearate, hydrogenated castor oil, hydrogenated vegetable oil, light mineral oil, mineral oil, polyethylene glycol, sodium benzoate, sodium lauryl sulfate, sodium stearyl fumarate, talc and zinc stearate. The amount of the lubricant may vary depending on various factors as would be known or can be determined by those skilled in the art.

As used herein, the term "disintegrant" is intended to encompass disintegrants known to those skilled in the art. The following is a list of non-limiting example embodiments of disintegrants that may be used in accordance with various embodiments herein: microcrystalline cellulose, sodium starch glycolate (e.g., Explotab®), croscarmellose sodium (e.g., Ac-Di-Sol®, Primellose®), crospovidone (e.g., Kollidon®, Polyplasdone®), magnesium aluminum silicate, polacrilin potassium, pregelatinized starch, sodium alginate, and starch. The amount of the disintegrant may vary depending on various factors as would be known or can be determined by those skilled in the art.

As used herein, the term "super-disintegrant" is intended to encompass super-disintegrants known to those skilled in the art. The following is a list of non-limiting example embodiments of super-disintegrants that may be used in accordance with various embodiments herein: croscarmellose sodium, crospovidone, and sodium starch glycolate. The amount of the super-disintegrant may vary depending on various factors as would be known or can be determined by those skilled in the art.

As used herein, "extract" or "herbal extract" refers to an extract from a plant, tree, bush, shrub, or other botanical organism, which may be used to impart a positive health benefit when administered to a subject. Extracts may be formed using any suitable technique known to those skilled in the art. By way of non-limiting example, extracts of Harpagophytum procumbens (Devil's claw), may be formed according to the methods set forth in U.S. Pat. Nos. 6,280,737 or 6,197,307.

As used herein, "an effective amount" refers to an amount of the specified constituent or of an overall composition (such as a tablet, granule, powder, etc.) that is effective in attaining the purpose for which the constituent or composition is provided. Therefore, an effective amount of a composition would be an amount suitable for relieving pain in the mammal to which the composition is administered.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

Depending on the composition or formulation, other excipients may be used as would be apparent to those skilled in the art. For example, as discussed further below, example compositions may include tablets, which may be coated on the outside for easier swallowing by a mammal. If tablets or other formulations are produced without a coating, it may be desirable to add one or more flavoring agents for example, as would be apparent to those skilled in the art. By way of further example, liquid compositions for example, may require one or more carriers.

Example embodiments are directed to therapeutic compositions or formulations that include natural ingredients for the treatment of pain in mammals. In particular, according to non-limiting example embodiments, compositions provided herein may include one or more core ingredients, and optionally one or more synergistic ingredients.

As discussed above, example core ingredients may include one or more (or all) of the following core ingredients, boswellia serrata, harpagophytum procumbens (devil's claw), turmeric, white willow and phellodendron amurense. Thus, non-limiting example embodiments are directed to therapeutic compositions that include boswellia serrata, harpagophytum procumbens, turmeric, white willow and phellodendron amurense.

Also encompassed by the term "core ingredients" are ingredients that provide the same or similar active components as the indicated core ingredients. By way of non-limiting example, boswellia serrata is a source of boswellic acid, which may provide relief from pain and inflammation. Other sources of boswellic acid may include for example, extracts of: Boswellia bhau-dajiana, Boswellia frereana, Boswellia papyrifera, Sudanese Boswellia sacra, and Boswellia carterii, Commiphora incisa, Commiphora myrrha, Commiphora abyssinica, Commiphora erthraea, Commiphora molmol, and Bursera microphylla, may be used as a substitute for or in conjunction with boswellia serrata, and are also encompassed by the term "core ingredients". An extract providing the boswellic acid preferably comprises in the range from about 20% to about 40% (could be up to 65%) by weight of the dose.

According to other example embodiments, "core ingredients" may include one or more additional or different ingredients than those listed above, such as one or more synergistic ingredients or other natural ingredients. Thus, additional compositions encompassed hereby may include boswellia serrata, harpagophytum procumbens, turmeric, white willow, phellodendron amurense, and at least one additional core ingredient.

According to example embodiments, the present compositions may additionally include one or more synergistic ingredients. As indicated above, the term "synergistic ingredient" is intended to encompass natural ingredients that are not necessarily "core ingredients" in the present compositions. Non-limiting example embodiments of possible synergistic ingredients include one or more (or all) ingredients selected from Chiococca Alba, Dihydroxybergamottin, Lactuca Virosa, Mimosa Pudica, Naringen, Paullinia Tomentosa, and Yerba Mate. Further example compositions include all of the following synergistic ingredients Chiococca Alba, Dihydroxybergamottin, Lactuca Virosa, Mimosa Pudica, Naringen, Paullinia Tomentosa, and Yerba Mate. According to non-limiting example embodiments, Ulmus Glabra may be a synergistic ingredient, for example as a substitute for Paullinia Tomentosa.

According to non-limiting example embodiments, the "core" ingredients may be added to the composition in approximately equal weight amounts. By way of example, the core ingredients may be present in the composition generally in an amount of about 25 to about 100 mg, or in an amount of about 30 to about 70 mg each or about 50 mg each. This amount may vary however, depending for example on the particular ingredient. For example, white willow may be present in an amount up to 240 mg per pill, or 5-17 weight % but this may also vary depending on the composition of the blend, adding or subtracting ingredients, which may increase or decrease the total mg dose and weight of the tablet. According to further embodiments, the synergistic ingredients may also be added in approximately equal weight amounts, which may be for example about 25 to about 100 mg, or about 30 to about 70 mg each, or about 50 mg each. But each ingredient may vary in amount such that it is present for example, in an amount of about 5-40 weight percent of the tablet.

According to example embodiments, the dose of core ingredients, synergistic ingredients, and active ingredient in the present formulations may vary up to about 200, 100 or 50 mg. Dosages may be determined by those skilled in the art.

Non-limiting example embodiments are directed to tablet compositions that include approximately 50 mg each of the following core and synergistic ingredients formed into an approximately 600 mg tablet for oral administration to a mammal.

Boswellia serrata;
Turmeric;
White willow;
Phellodendron Amurense;
Devil's claw (Harpagophytum Procumbens),
Paullinia Tomentosa (or optionally Ulmus Glabra);
Milkberry;
Mimosa Pudica;
Lactuca Virosa;
Naringen;
6-7 Dihydroxybergamottin; and
Yerba mate.

Each ingredient herein may be present in an appropriate extract, powder or other form for adding to the present compositions, as would be apparent to those skilled in the art.

Example compositions may include one or more excipients that may be selected, for example based on the type of composition being formed. Such excipient(s) may include for example, at least one excipient comprises at least one excipient selected from the group consisting of binders, fillers, diluents, lubricants, disintegrants, and super-disintegrants. By way of non-limiting example embodiment, the present compositions may include at least one excipient selected from the group consisting of microcrystalline cellulose, dextrose sodium starch glycolate, magnesium stearate, stearic acid, silica, and carnauba wax.

According to non-limiting example embodiments, mammals or patients may be directed to take for example two tablets (or other formulation) up to three times daily, depending for example on the weight of the mammal, symptom being treated, etc. Appropriate dosages may be determined by those skilled in the art.

According to non-limiting example embodiments, the present compositions help provide general analgesic relief of the pain associated with headaches, migraines, arthritis, toothaches, menstrual cramps, muscle aches, post operative surgical pain, strains, sprains, inflammation, chronic pain and other sources of pain.

Example compositions may include at least one additional drug or active ingredient that may be added to any of the present compositions, for example, to improve the ability of the present compositions to provide such pain relief. By way of non-limiting example embodiments, compositions herein may include one or more known natural or synthetic pain relievers or other drugs, such as NSAIDs, synthetic COX-2 inhibitors, etc. . . . By way of further example, such a pain reliever or other drug may include such drug in a smaller dosage than a typical formulation of such drug, to add some of the synergistic effect of the composition, while lessening potential side effects.

According to non-limiting example embodiments the compositions or formulations may be in the form of a tablet (which may be coated or uncoated). Other possible formulations may include capsules (hard or soft), liquid, powders, granules, suspensions, sachets, or additives to food substances or beverages, or even may be made into a tea, etc.

In embodiments in which the compositions are formed into tablets, the tablets formed herein can be at least partially or fully coated with a tablet coating composition known to those skilled in the art. An example coating may include one or more coating known to those skilled in the art, including, but not limited to, one or more of the following:
e.g., Surelease® (ethylcellulose), carnauba wax, cellulose acetate phthalate (CAP), cetyl alcohol, ethyl cellulose, gelatin, hydroxyethyl cellulose, hydroxypropyl cellulose, hydroxypropyl methylcellulose, microcrystalline wax, Opadry and Opadry II, polymethacrylates, polyvinyl alcohol, shellac, zein, Eudragit NE30D, Eudragit RS 30D, Eudragit RL30D, Methylcellulose, Cellulose Acetate Pthalate CAP), HPMCAS, Opadry, and Opadry II. According to non-limiting examples, a coating may be present in an amount of about 10% to about 20% by weight or in a thickness of about 10 to about 15 µm. The coating method may be performed by methods available to those skilled in the art.

Formulations, such as tablets, may be formulated into controlled release, immediate release, sustained release or extended release formulations.

Tablets in accordance herewith may weigh approximately 400 mg to about 800 mg or about 600 mg. Other tablet weights can also be used depending on ingredients and dosages desired, and depending on the mammal to whom the tablet is to be administered.

Example embodiments are also directed to methods of making the compositions or formulations herein. Such methods may include known tableting methods. A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant, sodium starch glycollate, cross-linked povidone, cross-linked sodium carboxymethyl cellulose) surface-active or dispersing agent. Moulded tablets may be made my moulding in a suitable machine a mixture of the powdered compound moistened with an inert liquid diluent.

By way of non-limiting example embodiment, tableting methods may include combining all or many of the ingredients (such as core, and/or synergistic ingredients and/or excipients) to form a mixture and compressing or compacting the mixture to form a tablet.

The present methods may further include adding a coating over the tablet according to techniques known to those skilled in the art. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

For preparing solid orally administered compositions such as capsules or tablets, the principal active ingredients may be mixed with at least one pharmaceutical carrier (e.g., conventional tableting ingredients such as cellulose, corn starch, lactose, sucrose, sorbitol, talc, stearic acid, magnesium stearate, dicalcium phosphate or gums) and other pharmaceutical diluents (e.g., water) to form a solid preformulation composition containing a substantially homogenous mixture of the composition of this invention, or a non-toxic pharmaceutically acceptable salt thereof. When referring to the preformulation compositions as substantially homogenous, it is meant that the active ingredients are dispersed reasonably evenly throughout the composition so that the composition may be readily subdivided into equally effective unit dosage forms such as capsules, pills and tablets. This solid preformulation composition can then be subdivided into unit dosage forms containing, for example, of the active-ingredient composition (which may include for example, the core ingredients or the core and synergistic ingredients).

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Also encompassed herein are methods of treating a mammal (including, but not limited to humans). Example methods include administering to a mammal in need thereof, an effective amount of a composition or formulation provided herein.

Such administration, for example in the case of tablets, is typically by oral administration to a mammal. Other forms of administration known to those skilled in the art are contemplated, depending on the formulation. By way of non-limiting example embodiment, other potential methods of administration may include methods known to those skilled in the art including, but not limited to, intraperitoneally, intravenously, orally, subcutaneously, intradermally, transdermally (e.g. pain patch), intramuscularly, intravascularly, endotracheally, intraosseously, intra-arterially, intravesicularly, intrapleurally, topically, intraventricularly, or through a lumbar puncture (intrathecally).

Formulations, such as tablets, may be used for treating mammals for a variety of different conditions. The present embodiments are generally to be used for the symptomatic relief of pain, such as minor to moderate acute pain (such as headaches, toothaches, menstrual cramps, muscle strains/sprains, inflammation etc). Thus, the compositions herein should be taken as directed until the pain is relieved. In a case of chronic pain (such as pain caused by osteoarthritis and rheumatoid arthritis, degenerative joint and disc disease), the present compositions may need to be taken for longer periods of time, but one must follow up with a physician for such uses, in order to minimize the potential for adverse events and to make sure that no other intervention is needed.

A recommended dosage for non-limiting example embodiments may include two tablets every 6-8 hours, or 3 times a day. Dosage may be adjusted however, (e.g., 3 at a time) to achieve desired affects; however, it is recommended that one should not exceed 6 tables in any given 24 hour period.

The herbal composition of this invention may be combined with a physiologically acceptable oral vehicle into unit dosages. A unit dosage may comprise a therapeutically effective amount of each herbal extract for a single daily administration (e.g., orally), or it can be formulated into smaller quantities of each ingredient to provide for multiple doses in a day. A unit dosage will depend upon many factors including age, size, and condition of the individual being treated and the number of times the unit will be taken in a single day. In any event, the entire daily dosage will be that which is physiologically acceptable to an individual and may be administered daily over a prolonged period of time.

The present compositions are unlike any other pain management product on the market. They combine the analgesic effect of natural opioid agonists with natural anti-inflammatories and also support gastro-intestinal health. Example compositions according to the present application are believed to be safer, more potent, and provide effective, lasting relief of pain from many conditions including for example, headaches, migraines, arthritis, toothaches, menstrual cramps, muscle aches, post operative surgical pain, strains, sprains, inflammation, chronic pain, etc.

The present compositions are presently believed to work by inhibiting damaged tissue from making prostaglandins. Prostaglandins are chemicals that allow one to feel pain. They are produced by the breakdown of arachidonic acid. By inhibiting prostaglandin production, the present compositions effectively decrease pain and inflammation.

As discussed further in the examples, below, to Applicants' knowledge, the present compositions are not associated with the adverse side effects of synthetic over-the-counter NSAID's and prescription pain relievers, such as COX-2 inhibitors.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

Example Composition

In this example, an herbal pain killer was formulated in accordance with example embodiments. This example provides an example of a blend of twelve specific medicinal herbs (five (5) core ingredients and seven (7) synergistic ingredients), in accordance with non-limiting example embodiments provided herein. Extensive research was performed by the present inventors on medicinal herbs and herbs with antioxidant qualities and those that may inhibit certain cytokines/mediators of pain and inflammation e.g. PGE2, COX-2, TNF, IL-1, etc. Twelve specific medicinal herbs were chosen and then processed utilizing specific manufacturing techniques. Typically the ingredients are purchased by the manufacturer from the raw materials distributor who has already performed any extracting and puts the ingredient in a form amenable to further processing, e.g. powder etc. to obtain a tablet of specific dosage.

According to examples herein the following twelve ingredients are combined in approximately 50 mg increments into an approximately 600 mg tablet:
Paullinia Tomentosa Extract (leaves); Milkberry Extract (leaves);
Mimosa Pudica Extract (whole plant);
Phellodendron Amurense Extract (bark);
Lactuca Virosa Extract (leaves);
White willow bark extract, 25% Salicin;
Turmeric Extract (rhizome);
Devil's claw (Harpagophytum Procubens);
Boswellia serrata extract (resin/gum) (e.g., 65% total acids);
Naringen (fruit);
6-7 Dihydroxybergamottin; and
Yerba mate extract 8%.

Additionally, the following excipients were included in the composition of this example:
Microcrystalline cellulose;
Dextrose;
Sodium starch glycolate;
Magnesium stearate;
Stearic acid;
Silica; and
Carnauba wax.

Example 2

Tablet Formulation of Herbal Pain Killer

In this example, the herbal pain killer of Example 1 was formulated into a tablet composition, which included approximately 50 mg each of the following ingredients formed into an approximately 600 mg tablet:
Paullinia Tomentosa Extract;
Milkberry Extract;
Mimosa Pudica Extract;
Phellodendron Amurense Extract;
Lactuca Virosa Extract;
White willow bark 25% extract;
Turmeric Extract;
Devil's claw;
Boswellia serrata extract;
Naringen;
6-7 Dihydroxybergamottin; and
Yerba mate extract 8%.

Also included in the present tablet formulation were the following excipients Microcrystalline cellulose; Dextrose; Sodium starch glycolate; Magnesium stearate; Stearic acid; Silica; and Carnauba wax.

The tablets were formed using common compression tableting techniques. The tablets were thereafter coated using well known coating techniques using a coating of Carnauba wax.

Example 3

Non-Randomized, Open Label, Efficacy Study

This example provides observational results of administering the composition of Examples 1 and 2, of twelve specific medicinal herbs, in a non-randomized, open-label study to evaluate the efficacy for the general relief of pain in healthy volunteers. The objectives of this phase II study were to determine if the composition of Examples 1 and 2 is effective at providing general relief of various types of pain and compare the subjective results participants obtained with this composition to other OTC or prescription pain relief products they commonly use, as well as describe any adverse events the participants experienced.

In this study various parameters were specifically evaluated. The present inventors found that the composition of Example 1 was just as effective if not better than the synthetic pain relievers typically utilized by the participants in most cases, was well tolerated and that most of the participants would not only recommend it to others but would utilize it as their primary pain reliever in the future. The inventors ultimately concluded that the composition of Example 1 is a safe and effective pain reliever and will become a very popular alternative to typical OTC and prescription pain relief products.

Extensive research was preliminarily done by the present inventors on medicinal herbs that may be utilized to treat conditions such as arthritis, menstrual cramps, headaches etc., as well as on herbs that had been known for their antioxidant qualities and for those known to inhibit certain cytokines/mediators of pain and inflammation e.g. PGE2, COX-2, TNF, IL-1 etc. The twelve specific medicinal herbs were chosen and then processed utilizing specific manufacturing techniques to obtain a tablet of specific dosage.

Study Population

Patients selected for inclusion in the trial were:
generally otherwise healthy and experiencing pain; acute or chronic;
*at least 16 years of age and able to complete a questionnaire capturing self-reported use of OTC/prescription analgesics for pain relief; and
able to comprehend and comply with requirements of the study.

(*Participants who were currently utilizing pain medication were advised to discontinue it during the study, unless medically contraindicated. Potential risks associated with concomitant use of multiple pain products were also explained in detail to participants prior to their inclusion.)

Patients were excluded from the trial if:
they had a participated in a study involving OTC/prescription pain relief products within the past 12 months;
they had a known allergy to any of the ingredients in the composition of Example 1;
if they were pregnant, trying to become pregnant, or breast-feeding;
they had previous treatment with herbal pain relief remedies with similar ingredients;
they had a medical condition, in the judgment of the examiner and/or study investigators, that may preclude the safe participation in the protocol or prevent completion of the study, such as: uncontrolled angina and/or congestive heart failure, severe chronic obstructive pulmonary disease, active treatment for cancer, major psychiatric disease, other systemic disease, or significant abnormalities of hematological, cardiac, pulmonary, metabolic, renal, hepatic, gastrointestinal or other systems;
they were currently using anti-coagulants (Coumadin, heparin, aspirin >325 mg day); or
they had a history of drug and/or alcohol abuse sufficient to hinder compliance with treatment or follow up procedures.

A total of 62 healthy volunteers completed the study. Patients in this trial had an age range of 16-77 years. There were 38 females, and 24 males. One group of 32 was required to take the composition of example 1 for at least 4 weeks for various pain related conditions e.g. degenerative arthritis, post-surgical etc. The remaining 30 were asked to take the composition of example 1 on an as needed basis for acute pain relief e.g. headaches, menstrual cramps, toothaches etc. Questionnaires were designed to assess how effective the composition of example 1 was at relieving their pain, and to compare it with other pain relievers they've taken in the past and also assess any adverse events. The following parameters were also assessed: pain severity (mild, moderate, severe), relief after using the composition of example 1 (poor, okay, good, amazing, revolutionary), onset of action (e.g. 20 min, 1 hr etc.), duration of relief, # of pills needed to achieve desired effect, adverse events/side effects, and if they would continue to utilize it and possibly recommend it to others.

Results

TABLE 1

Baseline Characteristics of Subjects

| Characteristic | Treatment Group |
|---|---|
| Age-yr | |
| Range | 16 77 |
| Sex-number (%) | |
| Female | 38 (61.3) |
| Male | 24 (38.7) |
| Pain Severity-number | |
| Mild | 5 |
| Moderate | 38 |
| Severe | 19 |
| Past Pain Reliever Use | |
| Advil | 10 |
| Aleve | 8 |
| Aspirin | 7 |
| Diclofenac | 1 |
| Ibuprofen | 28 |
| Imitrex | 1 |
| Methadone | 1 |
| Mobic | 1 |
| Nubaine | 1 |
| Naproxen | 2 |
| Oxycodone | 1 |
| Tylenol | 12 |
| Tylenol, Extra Strength | 4 |
| Ultram | 1 |
| Vicodin | 2 |

Cause of Painful Condition
Osteoarthritis of the spine, hip, knee, hands and shoulder
Rheumatoid arthritis
Chronic rotator cuff tears
Tendonitis
Menstrual cramps
Headaches (tension, migraine)
Muscle strains (cervical, lumbar)
General aches
Motor vehicle accident
High level sports related muscle soreness
Post Surgical A significant proportion of patients rated their pain as either moderate or severe, 61% and 31% respectively. Prior to entry in the trial patients consumed a wide variety of medications for their pain. Ibuprofen, Tylenol, including the extra strength variety, and Advil were the most widely used analgesics. On entering the trial, patients listed an assortment of reasons as the causative nature of their pain; these are listed in Table 1.

Relief Experienced w/ the composition of Example 1 by subjective pain scale
Mild Group:
Okay (2)
Good (2)
Amazing/Revolutionary (1)
Moderate Group:
Okay (3)
Good (10)
Amazing (20)
Amazing/Revolutionary (1)
Revolutionary (4)
Moderate/Severe Group:
Amazing (3)
Revolutionary (1)
Severe Group:
Poor (1)
Good (5)
Good/Amazing (1) Amazing (5)
Revolutionary (3)

FIG. 1 shows patient response to treatment with the composition of Example 1. Responders were asked to rate their level of pain relief after using the composition of Example 1 as either poor, okay, good, amazing or revolutionary. 56 (90.4%) of patients rated their response as good, amazing or revolutionary. Significantly, 45% of patients rated their response as either amazing or revolutionary. Overall response to treatment was similar when patients were assessed based on their initial assessment of pain rated as mild, moderate, or severe. Of all the patients followed only 1 patient (in the severe pain group) rated their response as poor. However, even in this group of patients with severe pain, 8 of 15 patients rated their pain relief as amazing or revolutionary while the remaining 6 patients rated their relief as good or amazing.

Figure 2:
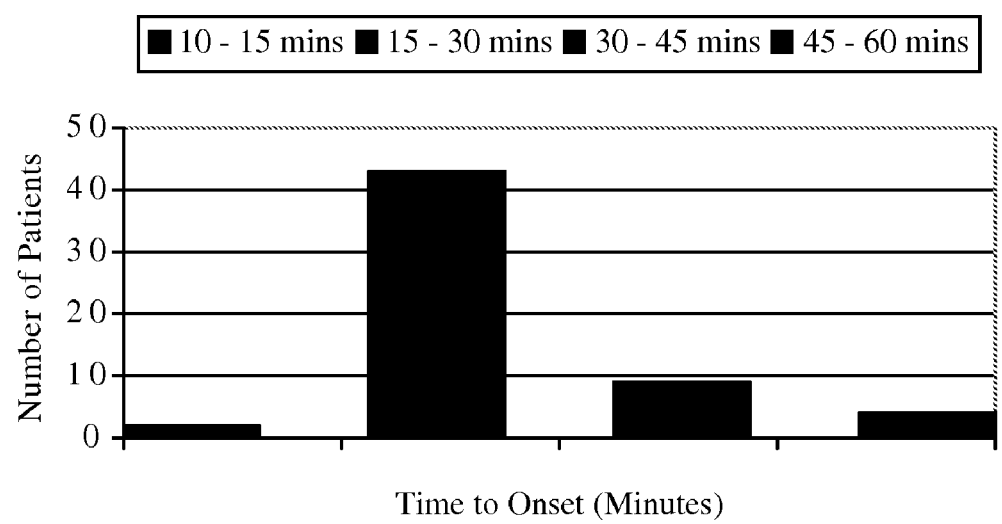
FIG. 2 is a graph showing the onset of action of the composition of Example 1.

Onset of Action ranged from 10 minutes to 1 hour with 76% experiencing relief within 30 minutes and the remaining 24% within the first hour. FIG. 2 is a graph showing the onset of action of the composition of Example 1. Most patients (76%) achieved pain relief within 30 minutes after dosing. Ninety four (94%) percent of patients achieved relief within 45 minutes and after 1 hour all patients reported having relief of pain.

10-15 min (3)
15 min (1)
15-30 min (1)
20 min (6)
20-30 min (7)
25 min (4)
25-30 min (4)
30 min (21)
30-45 min (2)
35 min (4)
40-45 min (1)
45 min (4)
45 min-1 hr (4)

Figure 3:
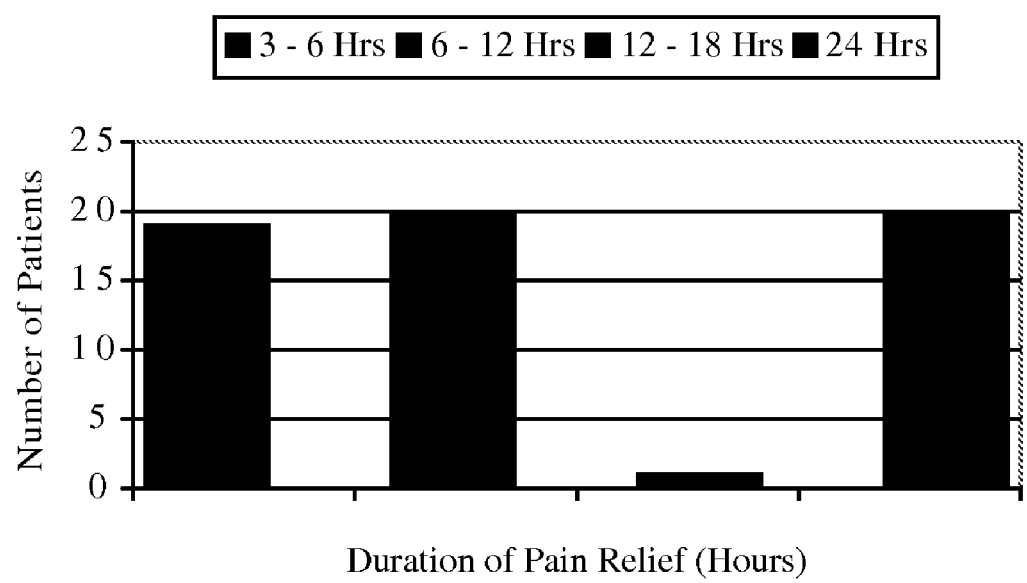
FIG. 3 is a graph summarizing the duration of pain relief achieved with use of the composition of Example 1.

FIG. 3 summarizes the duration of pain relief achieved with the use of the composition of Example 1. Duration of relief ranged from 3 hours to all day, with one even reporting relief of osteoarthritis pain for 4 days. Thirty-four percent experienced at least 6-16 hours of relief and thirty-three percent reported all day relief of symptoms.

3 hrs (2)
4 hrs (8)
4-5 hrs (2)
5 hrs (6)
5-6 hrs (1)
6 hrs (6)
6-8 hrs (3)
7 hrs (4)
8 hrs (5)
10 hrs (1)
12 hrs (1)
16 hrs (1)
All day (20)
4 days (1)
Discontinued (1)

Number of pills utilized to achieve desired effects ranged from 1 to 4 per dose.

| Patients | # of pills per dose |
| --- | --- |
| 3 | 1 |
| 23 | 2 |
| 14 | 3 |
| 22 | 4 |

*Reported adverse events/Side effects*
Constipation (1)**
Heartburn (1)
Sedation (1)
Abdominal cramping (1)***

*In the patients reporting adverse events all except the patient who experienced abdominal cramping still reported achieving amazing, okay, and okay relief of their pain complaints, respectively. Furthermore, 2 of the 3 would also consider taking the compositions of example 1 in the future and recommend it to others.

**This patient had a history of gastritis and was concomitantly taking ibuprofen despite our specifically advising her to discontinue it.

***This patient had a history of significant gastroesophageal reflux disease.

The composition of Example 1 was generally well tolerated with the only adverse events reported being single reports of constipation, heartburn, sedation and abdominal cramping, respectively.

The number of patients that indicated they would make the composition of Example 1 their primary pain relief choice and recommend to others was as follows Yes (58)
No (2)
Will use in combination with other meds (1)
Maybe (1)

Overall results were good to excellent in both treatment groups, e.g. 94% in the 4 week group and 90% in the acute pain group for subjective pain relief, average onset of action duration of relief and # of pills utilized.

Based on the results obtained from this study, the present example composition is surprisingly as effective if not more effective than the reported OTC and prescription NSAIDs and COX-2 inhibitors typically utilized by the consumers who participated in this study. Furthermore, the very low incidence of reported adverse events supports the historically excellent safety profiles of these particular ingredients. Overall the composition of Example 1 was shown to be both effective and safe.

The inventors acknowledge that this was not a randomized blinded study. However, as the information provided was given subjectively from volunteer participants who received no compensation, except free product during the study, potential bias is mitigated. The inventors are confident that based on its efficacy and safety, the composition of Example 1 will become a very attractive OTC natural pain relief alternative for consumers.

Example 4

Formation of Extracts

Some of the core and synergistic ingredients of the present application, may initially require being formed into an extract. An extract of certain ingredients is formed prior to mixing the ingredients to form a composition for administration to a mammal. This example provides a non-limiting example of how an extract may be formed from leaves.

Once leaves of a specific ingredient have been harvested, it may be desirable to reduce the leaves in size, for example leaf fragments, rather than adding to water (and/or other aqueous substances such as ethanol or methanol) as whole leaves. Those of ordinary skill in the art will recognize a variety of mechanisms for reducing the leaves to leaf fragments or bits, such as by chopping, cutting, crushing, tearing, slicing, etc., any of which may be suitably used. While the temperature of the cold water may vary, in some aspects, it may be less than about 25° C. Additionally, the amount of water (and/or other ingredient such as methanol or ethanol as would be apparent to those skilled in the art) with which the quantity of leaves is mixed may also vary.

Once the appropriate mixture ratio of leaves to water is obtained, the leaves of the mixture are then pulverized, in order to ruptured the cells of the tea leaves, and the mixture is maintained for an amount of time sufficient to release intracellular material from the leaves into the water and create an aqueous extract component and a leaf residue component. It should be understood that any method of pulverizing which physically ruptures the leaf cells, such as homogenizing, milling, grinding, chopping, blending, cutting, tearing, etc., may be used. A number of specific devices that may be suitably used to pulverized the tea leaves in the leaf and water mixture will be recognized by those of ordinary skill in the art, such as homogenizer, colloidal mills, stone mills, ball mills or tangential fluid energy mills. In accordance with the present method, the leaves in the leaf and water mixture may be subjected to various degrees of pulverization. However, in one aspect, at least about 75% of all leaf cells may be ruptured. In another aspect, at least about 80% to about 99% of all leaf cells may be ruptured.

The specific degree of pulverization, as well as other factors such as the exact type of plant used, the time of year at which the leaves were harvested, and the amount of time that the leaf and water mixture is maintained following pulverization, will determine the efficiency of the overall extract process.

Once the aqueous extract component has received a desired amount of intracellular material, the leaf residue component may be removed or separated from the aqueous extract component, and the aqueous extract component may then be collected. Those of ordinary skill in the art will recognize a number of ways in which the leaf residue component may be physically separated from the aqueous extract component, such as by centrifugation, super centrifugation, filtration, ultra filtration, etc., which do not require elevated temperatures, or any chemicals, such as solvents, etc.

After the aqueous extract component has been collected it may be used in the formation of compositions herein, or it may, optionally be further processed in order to create an extract formulation having desired characteristics. For example, in one aspect, after collection, the aqueous extract may be dried into a solid or a semi-solid state, such as a powdered form. Any of the various well known drying techniques, such as freeze-drying, or spray drying may be used. Additionally, various excipients may be added to the extract, either before or after drying, which may be required in order to provide a formulation with desired properties or forms, such as a powder, granule, tablet, capsule, etc. Those of ordinary skill in the art will recognize a number of excipients that may be suitably added, such as fillers, binders, sweeteners, flavors and other ingredients. Nearly any excipients that are known for use in the preparation of oral dosage pharmaceutical products, or natural supplement products, can be used. Examples of such excipients include without limitation, carbomer, carboxymethylcellulose sodium, cellulose, dextrin, dextrose, ethylcellulose, fructose, gelatin, guar gum, hydroxyethyl cellulose, hydroxypropyl cellulose, hydroxypropyl methylcellulose, glucose, maltodextrin, mannitol, methylcellulose, microcrystalline cellulose, polymethacrylates, povidone, sorbitol, starches, sucrose, sugar, sucralose, stevia, and flavor agents.

A number of agents may be included in the extraction process and the formulation of the present invention in order to improve the stability thereof by decreasing degradation of polyphenols, chlorophyll, or other beneficial ingredients, provided by the plant, such as L-theanine, tannins, vitamins, amino acids, minerals, proteins, and soluble fiber. Non-limiting examples of such agents which may be used include without limitation, may include vitamin C, or its derivatives, vitamin E or its derivatives, grape seed and its extract, wine and fruit polyphenols, beta-carotene, co-enzyme Q-10, alpha lipoic acid, N-acetyl cysteine, ascorbyl palmitate, butylhydroxinon, butylated hydroxyanisole (BHA), butylated hydroxytoluene (BHT), citric acid, calcium lactate, dodecyl gallate, erythorbic acid, fumaric acid, gallic acid, lactic acid, malic acid, magnesium lactate, octyl gallate, phosphoric acid, potassium citrate, potassium lactate, potassium tartrate, sodium ascorbate, sodium citrate, sodium erythobate, sodium lactate, sodium metabisulfite, sodium phosphate, sodium tartrate. In a detailed aspect, the antioxidant may be vitamin C or a vitamin C derivative, vitamin E or a vitamin E derivative, citric acid or its derivative, gallic acid or its derivative, and malic acid.

Although the invention has been described in example embodiments, additional modifications and variations would be apparent to those skilled in the art. It is therefore to be understood that the inventions herein may be practiced other than as specifically described, for example with respect to the formulation type, tablet size, coating, excipients, etc. . . . Thus, the present embodiments should be considered in all respects as illustrative and not restrictive. Accordingly, it is intended that such changes and modifications fall within the present invention as defined by the claims appended hereto.

What we claim is:

1. A tablet composition comprising approximately 50 mg each of the following ingredients formed into an approximately 600 mg tablet for oral administration to a mammal: Boswellia Serrata; Turmeric; White Willow; Harpagophytum Procumbens, Phellodendron Amurense; Paullinia Tomentosa; Chiococca Alba; Mimosa Pudica; Lactuca Virosa; Naringin; 6',7'-Dihydroxybergamottin; and Yerba Mate.

2. The tablet composition of claim 1, further comprising at least one excipient.

3. The tablet composition of claim 2, wherein the at least one excipient comprises an excipient selected from the group consisting of a binder, a filler, a diluent, a lubricant and a disintegrant, the disintegrant consisting of one of microcrystalline cellulose, sodium starch glycolate, croscarmellose sodium, crospovidone, magnesium aluminum silicate, polacrilin potassium, pregelatinized starch, sodium alginate and starch.

4. The tablet composition of claim 2, wherein the at least one excipient comprises at least one excipient selected from the group consisting of microcrystalline cellulose, dextrose, sodium starch glycolate, magnesium stearate, stearic acid, silica, and carnauba wax.

5. A therapeutic composition for the symptomatic relief of human pain comprising Boswellia Serrata, Harpagophytum Procumbens, Turmeric, White Willow, Chiococca Alba, 6', 7'-Dihydroxybergamottin, Lactuca Virosa, Mimosa Pudica, Naringin, Paullinia Tomentosa, Yerba Mate and Phellodendron Amurense as ingredients in approximately equal amounts by weight of 25 to about 100 mg of each ingredient to form one of a tablet, a capsule and a pill.

6. The therapeutic composition of claim 5, wherein said Boswellia Serrata, Harpagophytum Procumbens, Turmeric, and Phellodendron Amurense are present in an amount of 25 mg to 100 mg each, and in which White Willow is present in an amount between 5-1.7 weight % of the tablet, capsule or pill.

7. The therapeutic composition of claim 5, further comprising at least one excipient.

8. The therapeutic composition of claim 7, wherein the at least one excipient comprises at least one excipient selected from the group consisting of a binder, a filler, a diluent, a lubricant, and a disintegrant, the disintegrant consisting of one of microcrystalline cellulose, sodium starch glycolate, croscarmellose sodium, crospovidone, magnesium aluminum silicate, polacrilin potassium, pregelatinized starch, sodium alginate and starch.

9. The therapeutic composition of claim 7, wherein the at least one excipient comprises at least one excipient selected from the group consisting of microcrystalline cellulose, dextrose, sodium starch glycolate, magnesium stearate, stearic acid, silica, and carnauba wax.

10. The therapeutic composition of claim 5, wherein said composition is in the form of a tablet.

11. The therapeutic composition of claim 5, wherein said composition further comprises at least one additional active ingredient.

12. A method of forming the therapeutic composition of claim 10, comprising mixing Chiococca Alba, 6',7'-Dihydroxybergamottin, Lactuca Virosa, Mimosa Pudica, Naringin, Paullinia Tomentosa, Yerba Mate, Boswellia Serrata, Harpagophytum Procumbens, Turmeric, White Willow and Phellodendron Amurense to form the therapeutic composition.

13. The method of claim 12, further comprising adding a coating over at least a portion of the tablet.

14. A method comprising: administering to a human for symptomatic relief of pain, one of a tablet, a pill and a capsule weighing 400 mg to 800 mg of a composition comprising approximately equal portions by weight of at least Boswellia Serrata, Harpagophytum Procumbens, Turmeric, White Willow, Chiococca Alba, 6', 7'-Dihydroxybergamottin, Lactuca Virosa, Mimosa Pudica, Naringin, Paullinia Tomentosa, Yerba Mate and Phellodendron Amurense as ingredients.

15. The method of claim 14, wherein the equal portions by weight of each ingredient are between 25 to 100 mg.

16. The method of claim 15, wherein said composition is in the form of a coated tablet.

17. A therapeutic composition for the symptomatic relief of human pain comprising Boswellia Serrata, Harpagophytum Procumbens, Turmeric, White Willow, Phellodendron Amurense, Chiococca Alba, 6',7'-Dihydroxybergamottin, Lactuca Virosa, Mimosa Pudica, Naringin, Paullinia Tomentosa, and Yerba Mate as ingredients in approximately equal amounts by weight of 25 to about 100 mg of each ingredient to form a tablet.

\* \* \* \* \*